United States Patent [19]

Treiber et al.

[11] Patent Number: 5,322,855

[45] Date of Patent: Jun. 21, 1994

[54] CHOLESTEROL LOWERING COMPOUNDS

[75] Inventors: Laszlo R. Treiber, Gillette; Doss, George A., Westfield; Byron H. Arison, Watchung, all of N.J.

[73] Assignee: Merck & Co., Inc., Rahway, N.J.

[21] Appl. No.: 980,900

[22] Filed: Nov. 24, 1992

Related U.S. Application Data

[63] Continuation-in-part of Ser. No. 963,142, Oct. 19, 1992, abandoned.

[51] Int. Cl.$^5$ ............... A61K 31/335; C07D 493/08
[52] U.S. Cl. .................................... 514/452; 549/363
[58] Field of Search ............... 549/363, 39; 514/452, 514/440

[56] References Cited

U.S. PATENT DOCUMENTS

| | | | |
|---|---|---|---|
| 5,026,554 | 6/1991 | Bartizal et al. | 549/363 X |
| 5,096,963 | 3/1992 | Blain | 524/765 |
| 5,102,907 | 4/1992 | Bergstrom | 514/456 |
| 5,132,320 | 7/1992 | Bergstrom et al. | 514/452 |

FOREIGN PATENT DOCUMENTS

| | | | |
|---|---|---|---|
| 0448393 | 9/1991 | European Pat. Off. | C12P 17/04 |
| 0450812 | 10/1991 | European Pat. Off. | C07D 493/08 |
| 0475706 | 3/1992 | European Pat. Off. | C07D 493/08 |
| 0494622 | 7/1992 | European Pat. Off. | C07D 493/08 |
| 9212156 | 7/1992 | World Int. Prop. O. | C07D 493/08 |

OTHER PUBLICATIONS

Cleary, "Further Synthetic Studies . . . ", Syn. Commun., vol. 19(546), pp. 737–744, 1989.
Garlaschelli et al., "Anhydrons Lanthanum Trichloride, . . . ", Tet. Let., vol. 31(40), pp. 5815–5816, 1990.
Singh, "Transannular Cyclization Reactions . . . ", J. Org. Chem., vol. 44(5), pp. 843–846, 1979.
Baxter et al., "Squalestatin 1, . . . ", J. Biol. Chem., vol. 267(17), pp. 11705–11708, 1992.
Dawson et al., "The Squalestatins, . . . I. Taxonomy, . . . ", J. Antibiotics, vol. 45(5), pp 639–647, 1992.
Sidebottom et al., "The Squalestatins, . . . II. Structure Elucidation", J. Antibiotics, vol. 45(5), pp. 648–658, 1992.
Vercek et al. "Neighboring Group Interaction . . . ", J. Org. Chem., vol. 44(10), pp. 1695–1699, 1979.

*Primary Examiner*—Marianne M. Cintins
*Assistant Examiner*—Michael B. Hydorn
*Attorney, Agent, or Firm*—Roy D. Meredith; Jack L. Tribble

[57] ABSTRACT

Zaragozic acids isolated from a culture of MF5465 have been subjected to photoreaction, then derivatized at the 4-keto position. The resulting derivatives are active as squalene synthetase inhibitors and are useful in the treatment of hypercholesterolemia.

5 Claims, 4 Drawing Sheets

L-740,790

CHOLESTEROL LOWERING COMPOUNDS

BACKGROUND OF THE INVENTION

The present application is a continuation-in-part of Merck Case 18867, U.S. Pat. No. 07/963,142, filed Oct. 19, 1992, now abandoned.

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase.

Squalene synthase (also known as squalene synthetase) is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylemthyl) phosphonates as inhibitors of squalene synthetase.

Recently certain nonphosphorous containing inhibitors of squalene synthetase have been isolated as natural products. These natural product inhibitors are described in copending patent applications Ser. No. 496,734 filed Mar. 21, 1990, Ser. No. 496,742 filed Mar. 21, 1990, now issued as U.S. Pat. No. 5,096,923, and Ser. No. 582,452 filed Sep. 13, 1990, now issued as U.S. Pat. No. 5,102,907. Semisynthetic analogs of these naturally occurring compounds have been reported in copending application Ser. No. 698,766 filed May 10, 1991. A need still remains for a more effective squalene synthetase inhibitor, i.e., one that provides a greater antihypercholesterolemic effect and exhibits a good safety profile.

The natural product inhibitors are tricarboxylic acids. The present applicants have now found that these natural products known as zaragozic acid A, zaragozic acid B and zaragozic acid C undergo a photochemical reaction yielding monocarboxylic derivatives of the zaragozic acids, which are potent cholesterol lowering agents. The present invention discloses esters of these monocarboxylic acids.

These monocarboxylic derivatives exist as equilibrium structures of zaragozic acid, of the structures (I), (II) and (III):

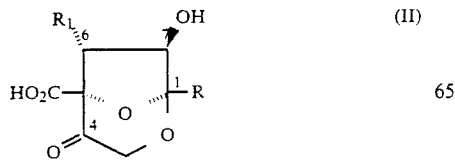

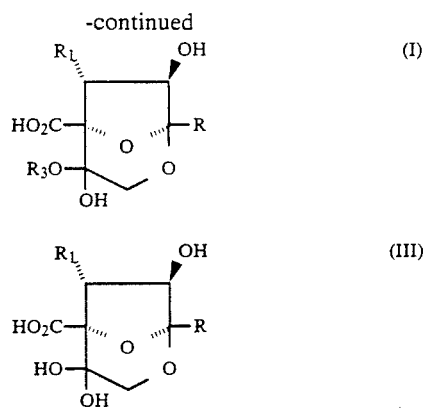

wherein and R, $R_1$ and $R_3$ are defined below.

Applicants disclose derivatives of equilibrium structures I, II and III, particularly the 4-keto structure II.

DETAILED DESCRIPTION OF THE INVENTION

Figure 1:
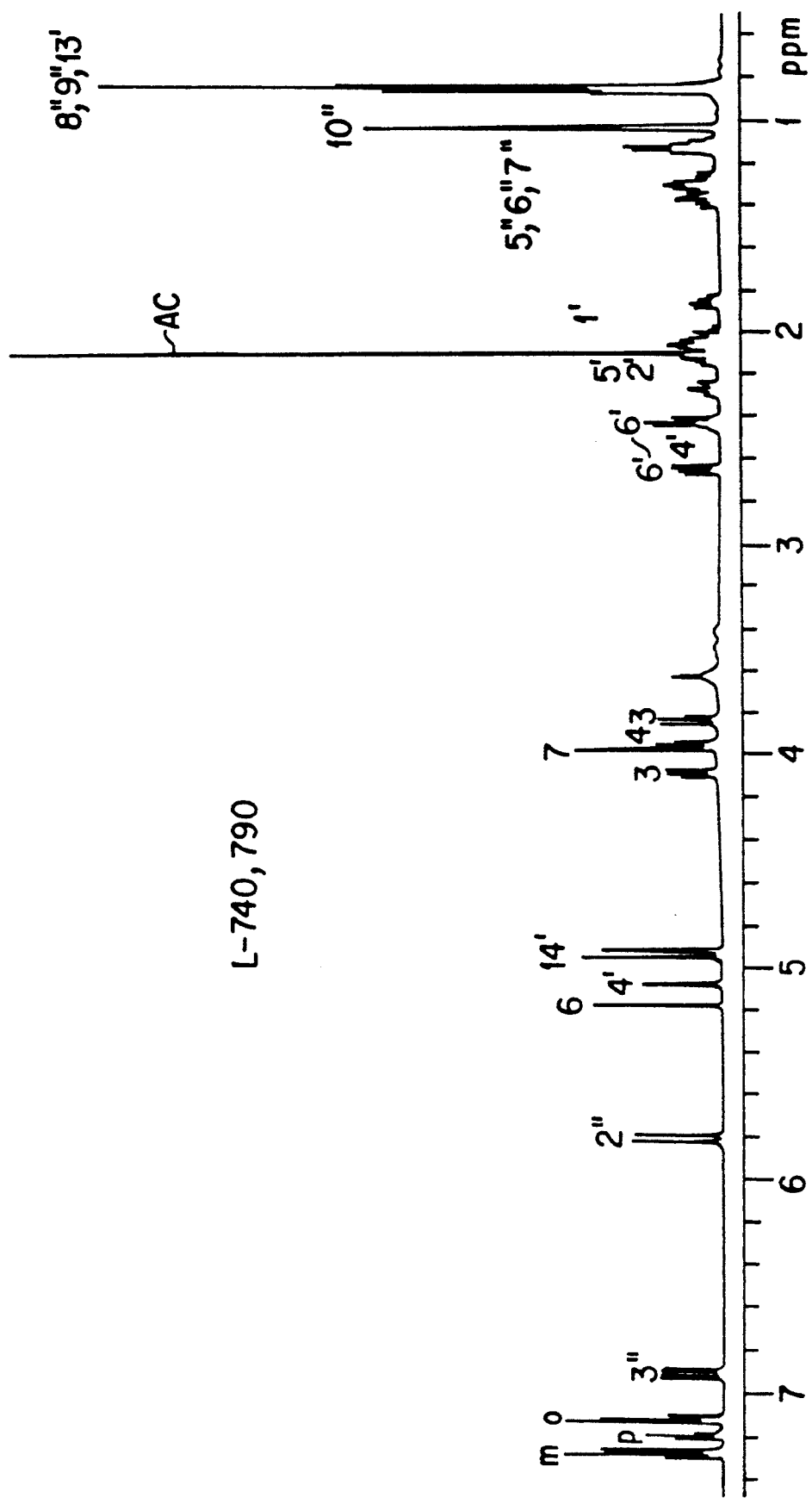
FIG. 1 is the $^1$H NMR spectra of L-740, 490 in $CDCl_3$.
Figure 2:
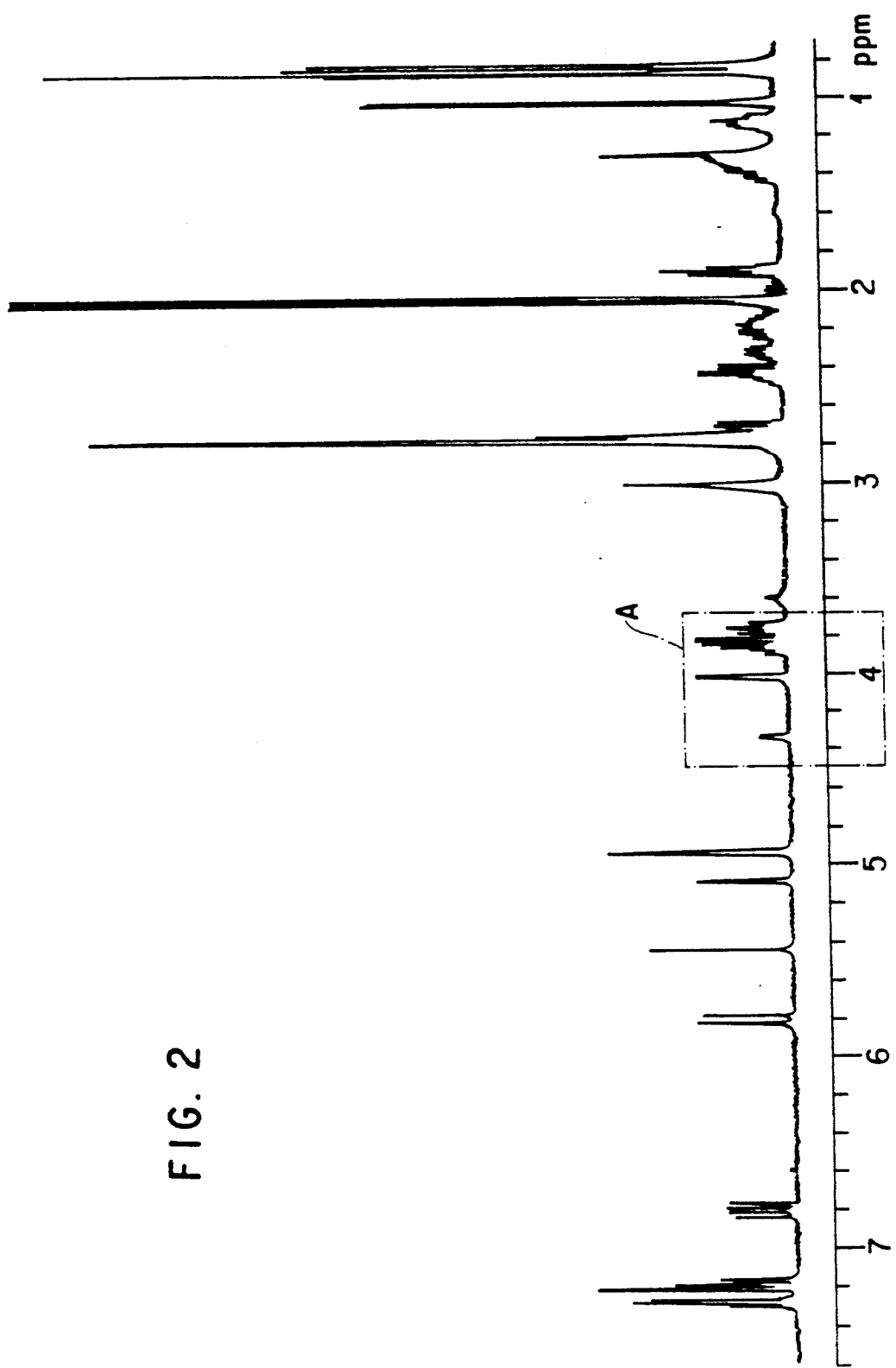
FIG. 2 is the $^1$H NMR spectra of L-740, 490 in acetone.
Figure 2A:
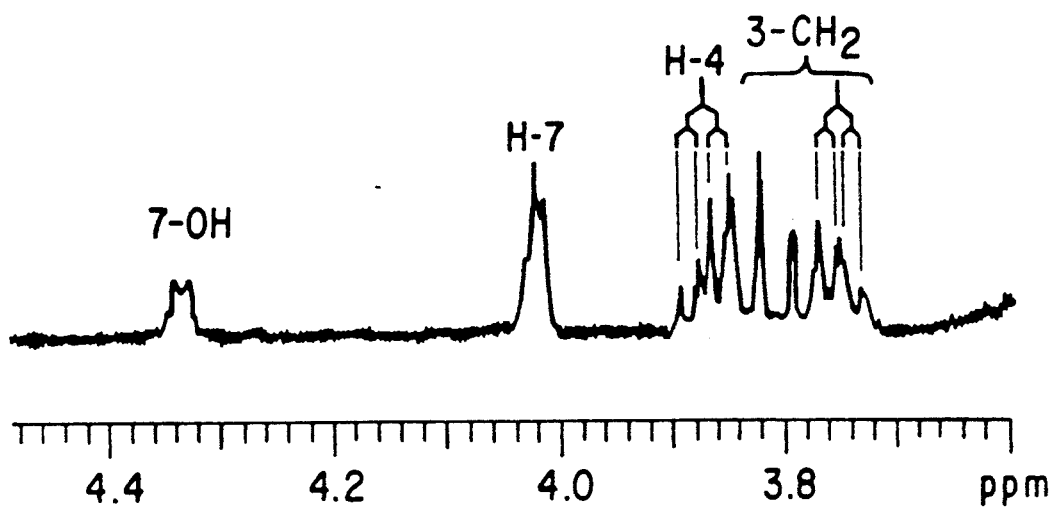
FIG. 2A is an expanded view of box A of FIG. 2.
Figure 2B:
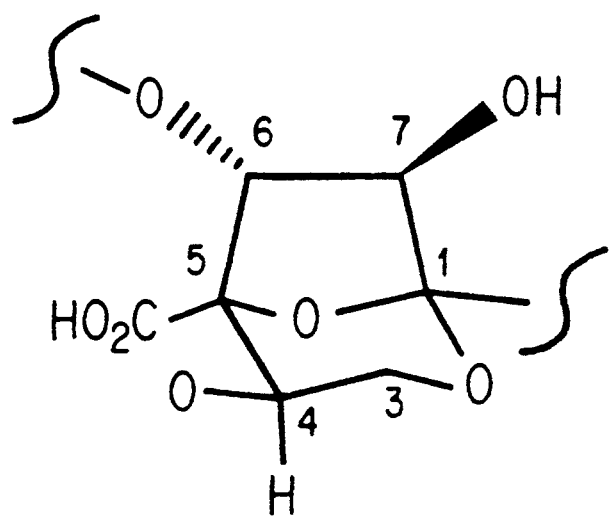
FIG. 2B illustrates the zaragozic acid heterocyclic core of L-740,790.
Figure 3:
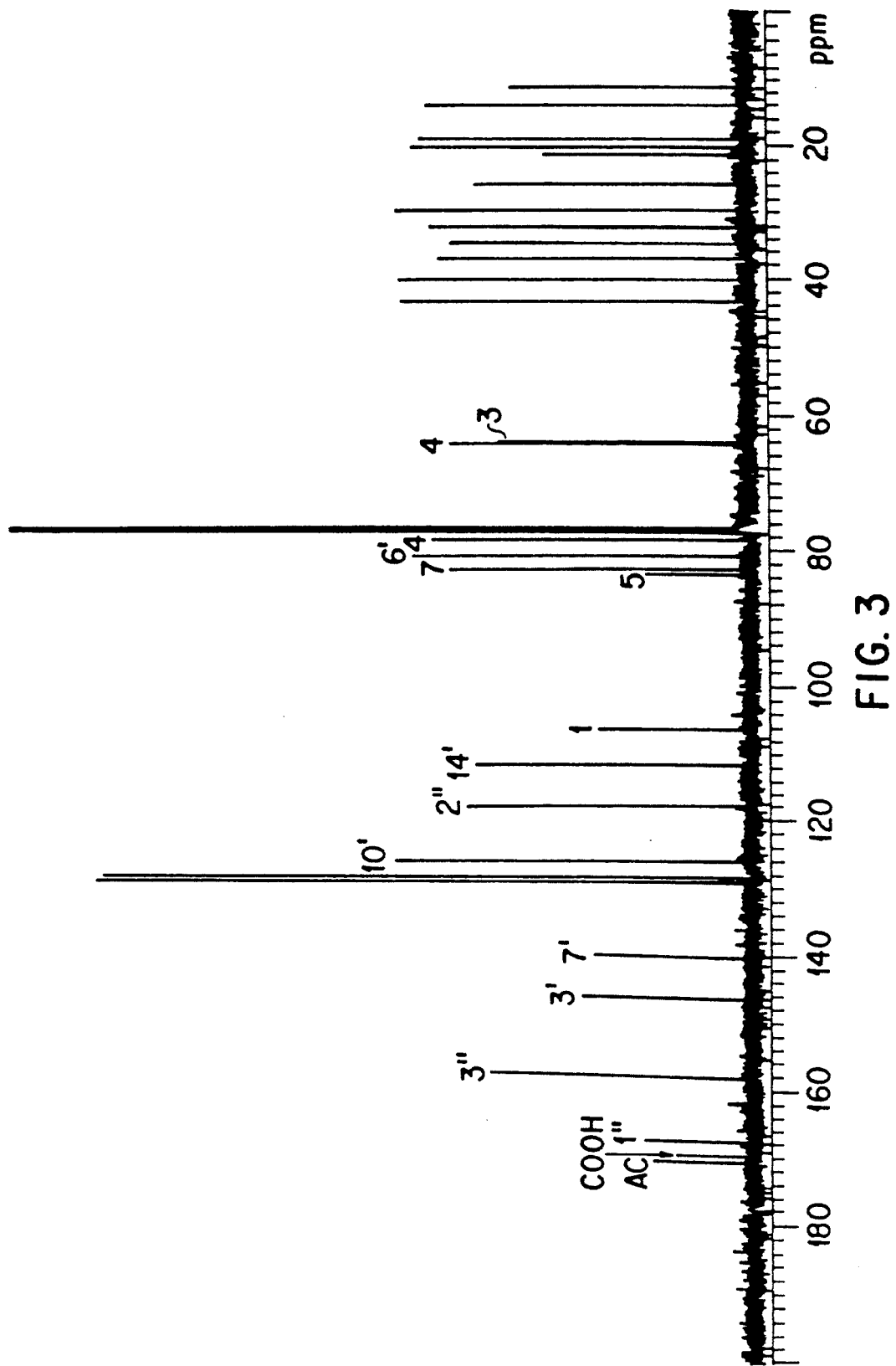
FIG. 3 is the $^{13}$C NMR spectra of L-740,490 in $CDCl_3$.

This invention relates to derivatives of the equilibrium structures I, II and III, particularly derivatives of II. The compounds of this invention have the structural formula V, defined as follows:

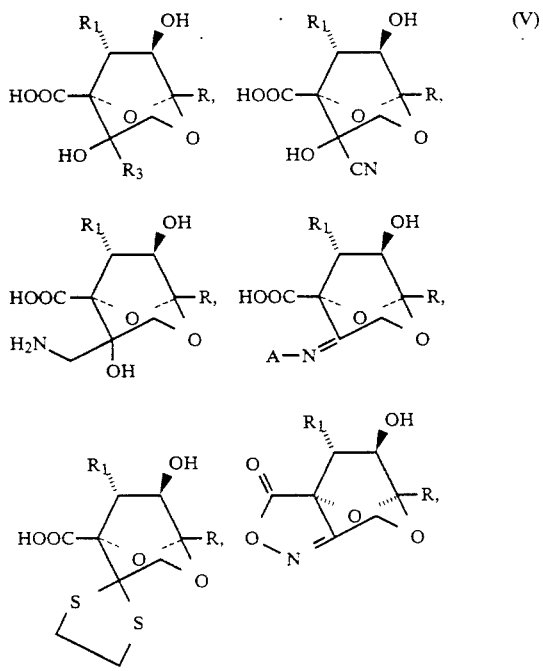

-continued

[Structural formulas showing cyclic compounds with R₁, OH, R substituents, including variants with HN-amide, HOOC with R₃S/SR₃, R₄-N=N with carbonyl, HOOC with R₃O/OR₃, and HOOC with HO/H groups]

wherein A is

—OR₃, —NHR₄, or —NH—N$\begin{matrix}R_3\\R_4\end{matrix}$ ;

R is selected from a) —CH₂—[structure with OR₂, CH=, and benzyl group];

b) —CH₂—[structure with OH, two methyls, CH=CH-phenyl]; or c) —CH₂—[structure with OR₂, methyl, benzyl]; and R₁ is selected from a) [structure with two methyl stereocenters, CH=CH, C(=O)O—];

b) $CH_3-CH=CH-(CH_2)_4-CH=CH-(CH_2)_4-\overset{O}{\underset{\|}{C}}-O-$ ; or c) [phenyl-(CH₂)₃-CH(CH₃)-CH=CH-(CH₂)₂-C(=O)O—]

R₂ is selected from
a) H and b) $CH_3-\overset{O}{\underset{\|}{C}}-$ ;

R₃ is H, C₁₋₄ alkyl;
R₄ is H, C₁₋₄ alkyl; or pharmaceutically acceptable salts thereof, provided that when R is —CH₂—[structure with OR₂, CH=, benzyl]

then R₁ is

[structure with two methyls, CH=CH, C(=O)O—];

and when R is —CH₂—[structure with OR₂, methyl, benzyl]

then R₁ is

[phenyl-(CH₂)₃-CH(CH₃)-CH=CH-(CH₂)₂-C(=O)O—]

and when R is

—CH₂—[structure with OH, methyls, CH=CH-phenyl]

then R₁ is $CH_3-CH=CH-(CH_2)_4-CH=CH-(CH_2)_4-\overset{O}{\underset{\|}{C}}-O-$ .

One embodiment of this invention is compounds further limited to the structural formulas:

[Four cyclic structures with R₁, OH, R, HOOC substituents: HOOC/HO/CN; HOOC/HO-N; carbonyl with O-N=; HOOC/HO-N/H]

A second embodiment is compounds further limited to the structural formulas:

[Two cyclic structures with R₁, OH, R, HOOC/HO-N= substituents]

-continued

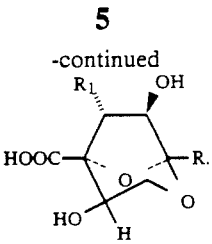

Another embodiment is the compound L-740,790, of the structure

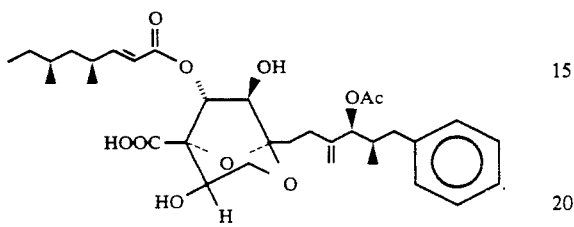

Compounds of the present invention are active as squalene synthase inhibitors and are useful as cholesterol lowering agents and anti-fungal agents.

Compound of formula (II) can be formed from zaragozic acid A (U.S. Pat. No. 5,096,963), zaragozic acid B (U.S. Pat. No. 5,132,320), and zaragozic acid C (U.S. Pat. No. 5,102,907) by photochemical treatment of the parent natural product, under exposure to air, followed by treatment with the appropriate reagent. Compounds of formulas (I), (II) and (III) wherein $R_2$ is acetate can be converted to compounds wherein $R_2$ is H by a biotransformation. A culture of MF6817 (ATCC 55189) has been employed in this transformation.

Compounds of formula (II) undergo a facile equilibrium to yield compounds of formula (I), in a $C_{1-5}$ alcohol such as methanol. In the presence of water they equilibrate to give compounds of formula (III). This equilibrium is established rapidly when the appropriate solvent is added to the material (II). However, the equilibrium may be shifted to predominantly structure (II) in acetone solution. The equilibrium may be shifted to predominantly structure (III) by the addition of water to the alcohol solution. Structure (I) is most predominant in the pure alcohol solution. Thus each structure I, II, or III may be obtained substantially free of the other structures. Substantially free should be understood to mean in a ratio of 80:20 or higher and more particularly with respect to (I) or (II) it may mean 90:10 or higher. Thus, the compound (I) substantially free of (II) and (III) should be taken to means that there is 10% or less of (II) and (III) present.

The compounds o the present invention may have asymmetric centers and may occur, except when specifically noted, as racemates, racemic mixtures or as individual diastereomers, or enantiomers, with all isomeric forms being included in the present invention.

When any variable (e.g., $R_3$, $R_4$, etc.) occurs more than one time in any constituent or in formula V, its definition on each occurrence is independent of its definition at every other occurrence. Also, combinations of substituents and/or variables are permissible only if such combinations result in stable compounds.

Formula V includes all eleven zaragozic acid nuclei, as defined above.

As used herein except where noted, "alkyl" is intended to include both branched- and straight-chain saturated aliphatic hydrocarbon groups having the specified number of carbon atoms. "Halogen" or "halo" as used herein, means fluoro, chloro, bromo and iodo.

The compounds of the present invention can be synthesized by the following methods.

In the schemes provided, Composition A is defined as the mixture of equilibrium structures (I).

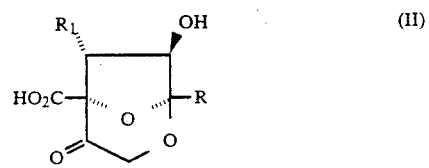

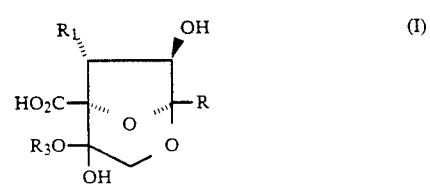

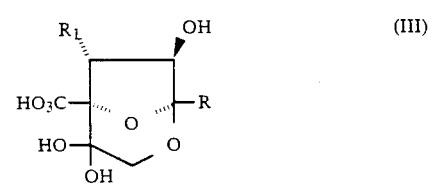

SCHEME 1

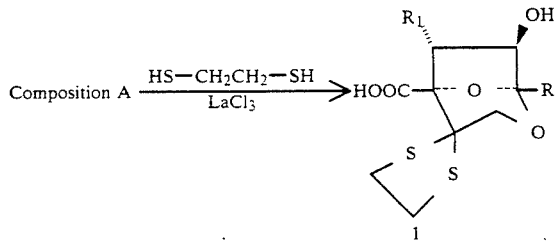

The 1,3-thiolane derivative 1 is readily prepared the commercially available anhydrous $LaCl_3$ as water scavenger. See also Garlaschelli, L. et al., Tetrahedron Lett. 31, 5815 (1990)

SCHEME 2

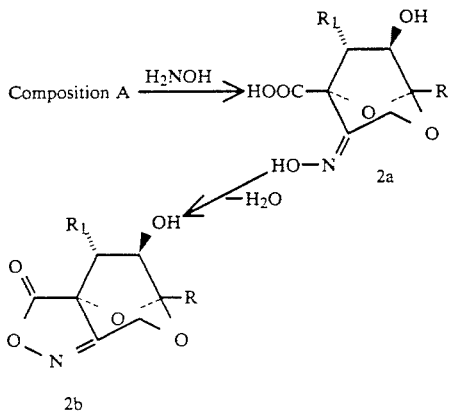

SCHEME 3

Composition A $\xrightarrow{H_2N-OR_3}$ 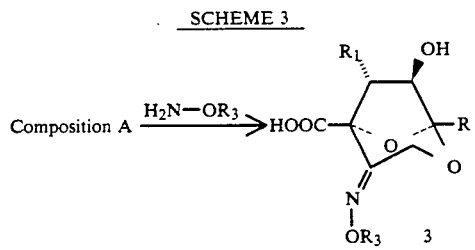

Reaction with hydroxylamine can yield the cyclized product 2. When $R_3$ is alkyl, O-alkyl oximes 3 are produced. See, for example, Singh, P., J. Org. Chem, 44, 843 (1979).

SCHEME 4

Composition A $\xrightarrow{R_3MgX}$ 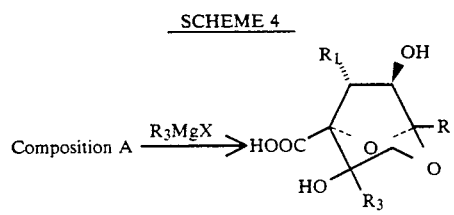

Reacting the 4-keto group with a Grignard reagent gives $R_3$ substituents at the 4-position.

SCHEME 5

Composition A $\xrightarrow{HCN}$ 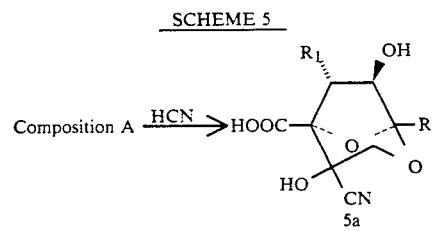

$\downarrow$ $H_2$/Reduction

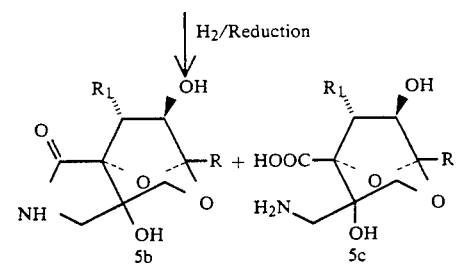

Reacting the keto group at the 4-position with nucleophile HCN gives an addition product 5a. Reduction gives the amine, which can cyclize (5b).

SCHEME 6

Composition A $\xrightarrow{H_2NNHR_4}$ 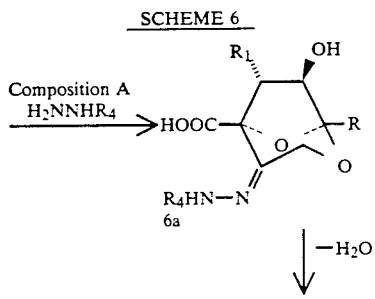

$\downarrow -H_2O$

-continued

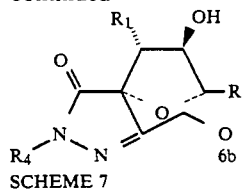

SCHEME 7

Composition A $\xrightarrow[\substack{R_3 \neq H; \\ R_4 \neq H}]{H_2N-N\substack{R_3 \\ R_4}}$ 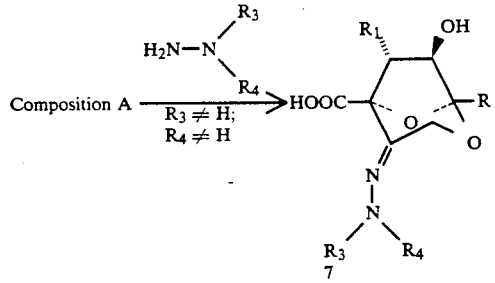

1,1-di-substituted hydrazines react with the carbonyl at the 4-position to give a hydrazone intermediate. When $R_3 \neq H$, and $R_4 \neq H$, the resulting substituted hydrazone 7 is formed. When $R_3 = H$, cyclization occurs, giving 6b.

SCHEME 8

Composition A $\xrightarrow{R_3-SH}$ 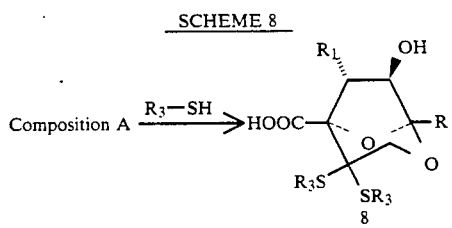

Reaction of composition A with alkylmercaptans gives 8. See, for example, Walker, Tetrahedron Lett. 4475 (1977).

SCHEME 9

Composition A $\xrightarrow{R_3O-CH\substack{OR_3 \\ OR_3}}$ 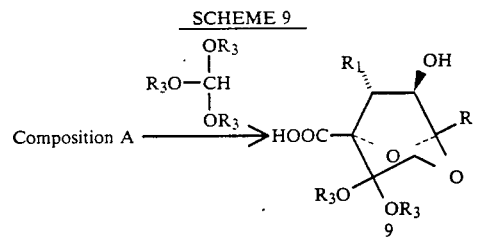

Reaction of composition A with an orthoformate ester in the corresponding alcoholic solvent gives 9.

SCHEME 10

Composition A $\xrightarrow{H_2/\text{reduction}}$ 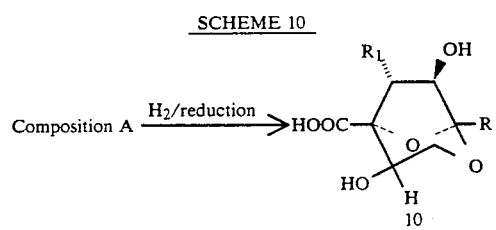

Reduction reduces the 4-Keto group to the corresponding alcohol. Reducing agents for Scheme 10 include but are not limited to $NaBH_4$, t-BuMgX, or aluminum triisopropoxide.

The present invention is also concerned with a method of treating hypercholesterolemia which comprises the administration to a subject in need of such treatment of a nontoxic therapeutically effective amount of a compound of formula V of the present invention, or mixture thereof, or a pharmaceutically acceptable salt thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but a daily dosage for adults is within a range of from about 20 mg to 2000 mg (preferably 20 to 200 mg) which may be given in two to four divided doses. Higher doses may be favorably employed as required.

The present invention is also concerned with a method of inhibiting squalene synthetase which comprises the administration to a subject in need of such treatment of a nontoxic therapeutically effective amount of a compound of formula V of the present invention, or mixture thereof, or a pharmaceutically acceptable salt thereof. Specifically, the compounds of this invention are useful in treating disease conditions such as, but not limited to, hypercholesterolemia conditions which require the action of the enzyme squalene snythetase. They may be administered by the same routes in the same dosages as described for the method of treating hypercholesterolemia.

The pharmaceutically acceptable salts of the compounds of this invention include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-CoA synthase inhibitors, and squalene epoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemgibrozil. Appropriate daily dosages for adults are niacin (2-8 gm), probucol (up to 1000 mg), clofibrate (up to 2 gm) and gemfibrozil (800-1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methy-(3-trimethylaminopropyl) iminotrimethylene dihalide]. The relative amounts of the compounds of this invention and these polymers is between 1:100 and 1:15,000.

The intrinsic squalene synthetase inhibitory activity of the compounds of this invention is measured by the standard in vitro protocols described below. The first assay measures activity against human squalene synthetase, the second against rat squalene synthetase.

HUMAN SQUALENE SYNTHETASE ACTIVITY

Preparation of Human HepG2 Cell Enzyme

1. SOURCE: HEPG2 CELL LINE (Liver, hepatoblastoma, Human) ATCC No. HB 8065
2. CELL GROWTH AND MAINTENANCE Culture Medium: Minimum essential medium (MEM) with non-essential amino acids, sodium pyruvate, and 10% fetal bovine serum. The medium was changed twice weekly. A confluent monolayer was achieved in 1 week. The growth medium is prepared as listed below.

| | Solution | Volume (mL) |
|---|---|---|
| 1. | MEM (Gibco #320-1090AK) With Earle's salts and L-glutamine | 1000 |
| 2. | Penicillin (10,000 units/mL), streptomycin (10,000 mg/mL), Gibco #600-5140 PG | 10 |
| 3 | MEM sodium pyruvate, 10 mM (100X) Gibco #320-1140 | 10 |
| 4. | MEM nonessential amino acids, 10 mM (100X) Gibco #320-1140AG | 10 |
| 5. | L-glutamine, 200 mM (100X), Gibco #320-5030AG | 10 |
| 6. | Hyclone fetal bovine serum, defined, Hyclone #A-111-L | 100 |

Subculture Procedure: Remove medium, wash with PBS, add fresh trypsin (0.25%)-EDTA (0.02%) with Hand's Balanced Salt solution and let flask stand for a minute and remove the trypsin solution. Incubate flask at 37° C. until cells detached. Add fresh medium, disperse and dispense cells into new flasks. Subcultivation ratio: 1:6.

PREPARATION of Delipidated Serum: Fetal calf serum (100 mL) and CAB-O-Sil (2 grams) stir overnight at 4° C. and centrifuge at 16,000 rpm for 5 hrs. Filter supernatant and store at 4° C.

48 hrs. prior to harvest, switch cells grown in MEM with 10% Fetal Calf serum to MEM with 10% delipidated serum.

Squalene Synthetase Assay

Reactions were performed in 1.2 mL polypropylene tube strips of 8. Buffer mixture and subtrate mixture for the assay were prepared from the following solution:

Buffer mixture contains 270 mM HEPES, pH 7.5, 20 mM Potassium fluoride and 5.4 mM Dithiothreitol(DTT). 55 μL of this mixture was used per assay. The final concentrations of HEPES, KF and DTT in the assay are 150 mM, 11 mM and 3 mM respectively.

| Substrate mixture: | | | |
|---|---|---|---|
| | Stock concentration | μL used per assay | Final concentration |
| 1. | MgCl$_2$, 20 mM | 10 | 6 mM |
| 2. | NADPH, 3 mM (made fresh) | 10 | 1 mM |
| 3. | Squalene Epoxidase inhibitor, Banyu FW-439H, 0.5 mg per mL | 0.02. | 1 μg per ml |
| 4. | $^3$H farnesylpyrophosphate, | 2.4 | 0.6 μM |

-continued

| | Substrate mixture: | | |
|---|---|---|---|
| | Stock concentration | µL used per assay | Final concentration |
| 5. | 25 mM, 20 Ci per mole Farnesyl-pyrophosphate, 3 mM | 0.08 | 2.4 µM |
| 6. | Water | 7.5 | |

3. Harvest: Remove medium, wash with PBS, add fresh trypsin (0.25%)-EDTA (0.02%) with Hank's Balanced Salt solution, rinse and remove. Incubate flash at 37° C. until cells detach. Add 6 mL of MEM medium per flash to suspend cells and combine into centrifuge tube. Spin cells at 1,000 rpm for 5 mins. Wash by resuspending cell pellet in PBS and repeat centrifuging. Count cells ($2.5 \times 10^9$ yield from 18 flasks (75 cm$^2$). Resuspend in 10 mL of 50 mM HEPES (N-[2-Hydroxyethyl]piperazine-N'-[2-ethane-sulfonic acid]) containing 5 mM MgCl$_2$, 2 mM MnCl$_2$, 10 mM DTT, pH 7.5 (enzyme suspension buffer).

4. Cell Extracts: Sonicate (probe sonicator setting #60, pulse) the cell suspension on ice for 2 min. After a 1 min. cooling on ice, the sonication is repeated until greater than 90% of the cells are broken as observed microscopically. Centrifuge cell suspension for 10 mins. at 10,000 rpm. Transfer supernatant to clean tube and centrifuge at 20,000 rpm for 20 mins. The HepG2 enzyme preparation was centrifuged at 34,000 rpm to separate the cytosol and microsomal enzymes. The enzyme suspension was diluted 1 to 1,536 and used to perform the squalene synthetase assay using 3 µM $^3$H-farnesyl pyrophosphate as the substrate.

For each reaction, 55 µL of buffer mixture was taken with 5 µL of an inhibitor solution in MeOH and 10 µL of diluted enzyme (1 to 1536 as described in the enzyme preparation; the final protein concentration of enzyme in the assay is 1.2 µg per mL.). The reaction was initiated by the addition of 30 µL of substrate solution and the mixture was incubated at 30° C. for 20 minutes. The reactions were stopped by the addition of 100 µL of 95% EtOH, vortexed, and 100 µL of a suspension of 1 gram per mL of Bio-Rad AG 1×8 resin (400 mesh, Chloride form) was then added, vortexed. 800 µL of heptane was added to each tube strip and the strips were capped and vortexed for 10 minutes.

RAT SQUALENE SYNTHETASE ACTIVITY

Preparation of Microsomes

Male Charles River CD rats (120 to 150 g) are fed a diet containing 0.1% lovastatin for 4 days. The livers from these rats were homogenized in 5 volumes (mL/g) of ice cold 50 mM HEPES (4-(2-hydroxy-ethyl)-1-piperazine-ethanesulfonic acid), 5 mM EDTA(ethylenediaminetetraacetic acid) pH 7.5 with a Potter-Elvehjem type tissue grinder. The homogenate is centrifuged twice at 20,000×g for 15 minutes at 4° C., discarding the pellet each time. The supernatant is then centrifuged at 100,000×g for 1 hour at 4° C. The resulting microsomal pellet is resuspended in a volume of the above homogenizing buffer equal to one-fifth the volume of the original homogenate. This microsomal preparation typically has a protein concentration of about 7 mg/mL. The microsomal suspensions are stored in aliquots at −70° C. Squalene synthetase activity in these aliquots is stable for at least several months.

Partial Purification of Prenyl Transferase

Prenyl transferase is purified to use in the enzymatic synthesis of radiolabelled farnesyl pyrophosphate. Prenyl transferase is assayed by the method of Rilling (Methods in Enzymology 110, 125-129 (1985)) and a unit of activity is defined as the amount of enzyme that will produce 1 µmole of farnesyl pyrophosphate per minute at 30° C. in the standard assay.

The livers of 23 forty-day old male rats that have been fed 5% cholestyramine plus 0.1% lovastatin are homogenized in a Waring blender in 1 liter of 10 mM mercaptoethanol, 2 mM EDTA, 25 µM leupeptin, 0.005% phenylmethyl sulfonyl fluoride pH 7.0 containing 0.1 trypsin inhibitor units of aprotinin/mL. The homogenate is centrifuged at 20,000×g for 20 minutes. The supernatant is adjusted pH 5.5 with 6N HOAc and centrifuged at 100,000×g for 1 hour. This supernatant is adjusted to pH 7.0 with 3N KOH and a 35-60% ammonium sulfate fraction taken. The 60% pellet is redissolved in 60 mL of 10 mM potassium phosphate, 10 mM mercaptoethanol, 1 mM EDTA pH 7.0 (Buffer A) and dialyzed against two 1 liter changes of Buffer A. This dialyzed fraction is applied to a 12.5×5 cm column of DEAE-sepharose 4B equilibrated with Buffer A. The column is washed with 700 mL of Buffer A and a 1 liter gradient from Buffer A to 100 mM potassium phosphate, 10 mM mercaptoethanol, 1 mM EDTA pH 7.0 . Fractions having a specific activity greater than 0.20 units/mg are combined, solid ammonium sulfate is added to bring to 60% saturation and pelleted. The pellet is dissolved in 8 mL of 10 mM Tris, 10 mM β-mercaptoethanol pH 7.0 (Buffer B). The redissolved pellet is taken to 60% saturation with ammonium sulfate by adding 1.5 volumes of saturated ammonium sulfate in Buffer B. This ammonium sulfate suspension typically contains 3.5 units/mL with a specific activity of 0.23 units/mg and is free of isopentenyl pyrophosphate isomerase activity. This ammonium sulfate suspension is used for the synthesis of [4-$^{14}$C]farnesyl-pyrophosphate and its activity is stable stored at 4° C. for at least 6 months.

Enzymatic Synthesis of [4-$^{14}$C]farnesyl-pyrophosphate

The solvent (ethanol: 0.15N NH$_4$OH, 1:1) is removed from 55 µCi of [4-$^{14}$C]isopentenyl pyrophosphate (47.9 µCi/µmole) by rotary evaporation. Six hundred microliters of 100 mM Tris, 10 mM MgCl$_2$, 4 mM dithiothreitol pH 7.5 is added and the solution is transferred to a 1.5 mL Eppendorf centrifuge tube. Geranyl-pyrophosphate, 250 µL of a 20 mM solution, and 50 µL of the ammonium sulfate suspension of prenyl transferase are added to initiate the reaction. This incubation contains 5 µmoles of geranyl pyrophosphate, 1.15 µmoles of isopentenyl pyrophosphate, 6 µmoles of MgCl$_2$, and 0.18 units of prenyl transferase in a volume of 900 µL. The incubation is conducted at 37° C. During the incubation, the mix typically turns cloudy white as the newly formed magnesium complex of farnesyl pyrophoshate precipitates out of solution. The [4-$^{14}$C]farnesyl pyrophosphate is collected by centrifugation for 3 minutes at 14,000 rpm in an centrifuge tube, the supernatant removed, and the pellet is dissolved in 1.0 mL of 50 mM HEPES, 5 mM EDTA, pH 7.5. The yield is typically about 50 µCi (90%) of [4-$^{14}$C]farnesyl pyrophosphate. The [4-$^{14}$C]farnesyl pyrophosphate is stored in aliquots at −70° C.

Squalene Synthetase Assay

Reactions are performed in 16×125 mm screw cap test tubes. A batch assay mix is prepared from the following solution:

| | | mL per assay | volume for 50 assays |
|---|---|---|---|
| 1. | 250 mM Hepes pH 7.5 | 20 | 1000 |
| 2. | NaF 110 mM | 10 | 500 |
| 3. | MgCl$_2$ 55 mM | 10 | 500 |
| 4. | Dithiothreitol 30 mM | 10 | 500 |
| 5. | NADPH 10 mM (made fresh) | 10 | 500 |
| 6. | [4-$^{14}$C]farnesyl-pyrophosphate 47.9 μCi/μmole, and 0.025 μCi/3.0 μL | 3.0 | 150 |
| 7 | H$_2$O | 24 | 1200 |

This assay mix is degassed under vacuum and flushed with N$_2$. Solutions of the squalene synthetase inhibitors are prepared either in DMSO or MeOH and a 1:120 dilution of the microsomal protein is made with the original homogenizing buffer. For each reaction, 87 μL of the assay mix is taken with 3 μL of an inhibitor solution (DMSO or MeOH in the controls), warmed to 30° C. in a water bath and then the reaction is initiated by the addition of 10 μL of the 1:120 dilution of microsomal protein (0.6 μg protein total in the assay). The reactions are stopped after 20 minutes by the addition of 100 μL of a 1:1 mix of 40% KOH with 95% EtOH. The stopped mix is heated at 65° C. for 30 minutes, cooled, 10 mL of heptane is added and the mix is vortexed. Two grams of activated alumina is then added, the mix vortexed again, the alumina allowed to settle and 5 mL of the heptane layer is removed. Ten mL of scintillation fluid is added to the heptane solution and radioactivity is determined by liquid scintillation counting.

Percent inhibition is calculated by the formula:

$$\left[1 - \left(\frac{[\text{Sample} - \text{Blank}]}{[\text{Control} - \text{Blank}]}\right)\right] \times 100$$

IC$_{50}$ values are determined by plotting the log of the concentration of the test compound versus the percentage inhibition. The IC$_{50}$ is the concentration of inhibitor that gives 50% inhibition as determined from these plots.

The present compounds are also useful as broad spectrum antifungal agents as determined by broth and agar dilution methods. Thus the present invention is also directed to a method of treating fungus infections which comprises the administration to an organism in need of such treatment a nontoxic therapeutically effective amount of a compound represented by the structural formula (V) and pharmaceutically acceptable salts thereof. Generally form 2 to about 20 mg/kg should be employed as a unit dosage in an antifungal treatment.

Furthermore the compounds of the present invention are useful as inhibitors of farnesyl-protein transferase and thereby of farnesylation of the RAS protein and thus block the ability of RAS to transform normal cells to cancer cells. Farnesyl-protein transferase activity may be reduced or completely inhibited by adjusting the compound dose.

The intrinsic farnesyl-protein transferase (FTase) activity of representative compounds of this invention is measured by the assays described below:

RASIT ASSAY I

Farnesyl-protein transferase (Ftase) from bovine brain is chromatographed on DEAE-Sephacel (Pharmacia, 0–0.8M NaCl gradient elution), N-octyl agarose (Sigma, 0–0.6M NaCl gradient elution ),and a mono Q HPLC column (Pharmacia, 0–0.3M NaCl gradient). Ras-CVLS at 3.5 μM, 0.25 μM [$^3$H]FPP, and the compounds to be assayed are incubated with this partially purified enzyme preparation.

RASIT ASSAY II

Farnesyl-protein transferase Ftase) from bovine brain is chromatographed on DEAE-Sephacel (Pharmacia, 0–0.8M NaCl gradient elution), N-octyl agarose (Sigma, 0–0.6M NaCl gradient elution), and a mono Q HPLC column (Pharmacia, 0–0.3M NaCl gradient). Ras-CVLS at 1.0 μM, 0.5 μM [$^3$H]FPP, and the compounds to be assayed are incubated with this partially purified enzyme preparation. The Ftase data is a measurement of the ability of the test compound to inhibit Ras farnesylation in vitro.

The pharmaceutical compositions containing the compounds of structural formula V inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carries, e.g. saline, at a pH level, e.g. 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal a day.

EXAMPLE 1

Preparation of a composition of (I), (II) and (III) etc. wherein

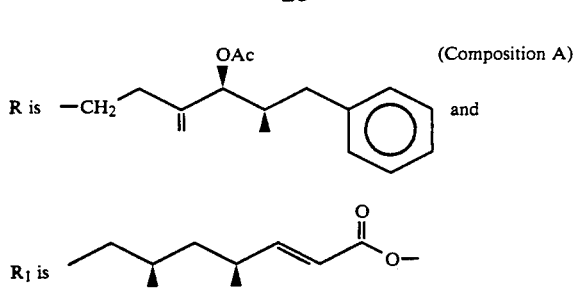

(Composition A)

R is —CH₂—... and

R₁ is ...

Step A  Preparation of Zaragozic Acid A

1. Culturing MF5453

Culture MF5453 (ATCC 20986) was inoculated into KF seed medium using one glass scoop of the original soil tube. The KF seed flask was incubated for 73 hours at 25° C. , 220 rpm, 85% humidity. At the end of this incubation, 2.0 mL aliquots were aseptically transferred to each of 75 MBM production medium flasks. These production flasks were then incubated at 25° C., 220 rpm, 85% humidity, with a fermentation cycle of 14 days. Flasks were harvested as follows: mycelial growth was homogenized for 20 seconds at high speed using Biohomogenizer/mixer (Biospec Products Inc. Bartlesville, Okla.); and then 45 mL methanol was added to each flask (final methanol concentration was approximately 50%). Flasks were then returned to the shaker and agitated at 220 rpm for 30 minutes. Subsequently, the contents of the flasks were pooled.

2. Isolation of Compound Zaragozic Acid A

A 6 liter 50% methanol homogenized fungal extract exhibiting a pH of 4.5 was employed in the following isolation procedure. The mycelia were filtered through celite and the recovered mycelial cake was extracted again by stirring overnight with 3 L of 50% methanol and again filtered.

The combined extract (9 L) of 50% methanol was diluted to 25% methanol with water (total volume 18 L) and applied to a Mitsubishi HP-20 column (750 mL) at a flow rate of 80 mL/minute. The column was washed with water (1 L) and eluted with a stepwise gradient of methanol consisting of 50/50 methanol/H₂O (1 L), 60/40, methanol/H₂O (1 L), 80/20 methanol/H₂O (2 L), 90/10 methanol/H₂O (1 ), 100% methanol (2 L), and 100% acetone (1 L). The fractions from 50/50 to 90/10 methanol/H₂O were combined and diluted with water to 35/65 methanol/H₂O (total volume 10 L).

The 10 L of 35/65 methanol/H₂O was acidified with 1.0N HCl (20 mL) to pH 3.0 and extracted into EtOAc (4 L). The EtOAc layer was separated and the solvent removed in vacuo to yield 260 mg of an orange oil.

A portion (10%) of the orange oil was dissolved in 1 mL methanol and diluted with 0.8 mL 10 mM potassium phosphate (pH 6.5) with some precipitation. The suspension was applied to a preparative HPLC column (Whatman Magnum 20 C₁₈, 22 mm ID×25 cm, 8 mL/minute. The initial mobile phase was 60/40 methanol/10 mM K₃PO₄, pH 6.5, and after 20 minutes the mobile phase was changed to 80/20 methanol/10 mM potassium phosphate, pH 6.5. Fractions of 8 mL each were collected, and the fractions from 31 to 33 minutes were combined, diluted with water to 35% methanol, acidified with 10% HCl to pH 3, and extracted into EtOAc. The solvent was removed in vacuo and a clear slightly yellow oil identified as Zaragozic Acid A was obtained.

| KF SEED MEDIUM | per liter | Trace Elements Mix | g/L |
|---|---|---|---|
| Corn Steep Liquor | 5 g | FeSO₄—7H₂O | 1.0 |
| Tomato Paste | 40 g | MnSO₄—4H₂O | 1.0 |
| Oat Flour | 10 g | CuCl₂—2H₂O | 0.025 |
| Glucose | 10 g | CaCl₂—2H₂O | 0.1 |
| Trace Element Mix 10 mL | | H₃BO₃ | 0.056 |
| pH adjusted to 6.8 (presterile) | | (NH₄)₆Mo₇O₂₄—4H₂O | 0.019 |
| 50 mL/nonbaffled 250 mL Erlenmeyer flask | | ZnSO4—7H₂O | 0.2 |
| autoclave 20 minutes (121 C. 15 psi) | | dissolved in 1 L 0.6 N HCl | |

| MBM Products Medium | g/L | Medium #2 Ingredients | g/L |
|---|---|---|---|
| Malt extract (Difco) | 5.0 | | |
| Glucose | 15.0 | Dextrose | 4.0 |
| Peptone | 1.0 | Malt Extract (Difco) | 10.0 |
| KH₂PO₄ | 1.0 | Yeast Extract | 4.0 |
| MgSO₄ | 0.5 | Nutrient Broth | 4.0 |
| distilled H₂O | 1000.0 mL | pH 7.0 | |
| (no pH adjustment) 45 mL/nonbaffled 250 mL Erlenmeyer flask autoclave 15 minutes (121 C., 15 psi) | | | |

Step B  Preparation of Composition A

A solution of 2.5 mg/mL of Zaragozic acid A in DMSO was prepared and 30 mL aliquots of this solution were placed in each of five 250 mL Erlenmeyer flasks. The samples were placed in a 37° C. incubator at a distance of 25–30 cm from a fluorescent light and were exposed to air. The reaction was allowed to continue for 6–8 days prior to isolation.

Step C  Isolation of Composition A

The five samples from Step B were combined and mixed with water (200 mL). The solution was acidified with citric acid and extracted twice with 100 mL portions of CH₂Cl₂. The combined methylene chloride phases were evaporated to an oily residue that was transferred to test tubes and evaporated further to dryness in a stream of nitrogen at 40°–50° C. The dry residues were redissolved in small volumes of methanol and combined. The methanol solution (10–15 mL) was mixed with formic acid (0.5 mL) immediately before being loaded onto a HP-20 column (2.5×23 cm, 113 mL) equilibrated with 0.5% formic acid in water. The chromatogram was developed in a stepwise gradient made using 200 mL of each solvent mixture of water-acetonitrile beginning with volume ratios of 100:0, 90:10, etc. in 10% increments up to 0:100. Each mixture contained 7 mL of formic acid. The flow rate was 3 mL/minute. The bulk of product was found in the range of 1500–1615 mL of eluate. The samples were evaporated to dryness and then redissolved in methanol to 20 mg/ml concentration used in preparative HPLC. The final purification was by preparative HPLC carried out on a Beckman Ultrasphere ODS (10×250 mm) column using 0.1% formic acid in acetonitrile—water (60:40 v/v) as eluant at a flow rate of 4.00 mL/min and a detector setting of 213 nm. The retention time of compound IA was found to be 15.8 minutes; for comparison the retention time of zaragozic acid A was 10.4 minutes.

¹H NMR (400 MHz) (Acetone) IIA 4.67 (d, 17.1, 1H), 4.42 (d, 17.1, 1H) 3-CH₂ IA 4.16 (d, J=12.1, 1H), 3.71 (d, 12.1, 1H) 3-CH₂ IIIA 4.11 (d, 13.4, 1H), 3.91 (d, 13.4, 1H) 3-CH₂

EXAMPLE 2

Preparation of the (C-4) 1,3-dithiolane derivative of Composition A, comprising a compound of the structure

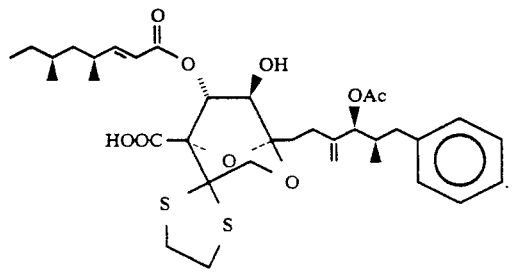
(IIB)

According to Garlaschelli et al., Tetrahed. Lett. 31, 5815 (1990), anhydrous La Cl₃ (2 mmol) and 1,2-ethanethiol (4 mmol) are added in that order, to a stirred anydrous CH₂Cl₂ solution (2 mL) of composition A (0.1 mmol). The reaction is carried out at room temperature in Ar atmosphere. The total reaction time is 3 days. After the reaction the mixture is filtered and evaporated to dryness.

The dry residue is redissolved in acetonitrile (2 mL) and loaded onto an HP-20 column (2.5×22.5 cm, 110 mL) equilibrated with 0.5% formic acid in water. The column is eluted in the stepwise gradient mode first with 0.5% formic acid in water then in 0.5% formic acid in water—acetonitrile mixtures of increasing acetonitrile concentrations. The fractions containing the product are located by means of analytical HPLC and combined. The sample is evaporated to dryness. The residue is redissolved in methanol (1 mL). The solution obtained is subjected to final purification by means of preparative HPLC on a Beckman Ultrasphere ODS semiprep. column (10×250 mm). A linear gradient is used for the preparative HPLC chromatography with 0.1% formic acid in water (solvent A) and 0.1% formic acid in acetonitrile (solvent B).

EXAMPLE 3

Preparation of the (C-4) oxime of composition A, comprising a compound of the structure

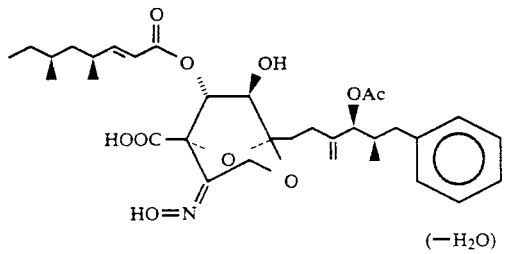
(IIC)

(—H₂O)

and its cyclic form:

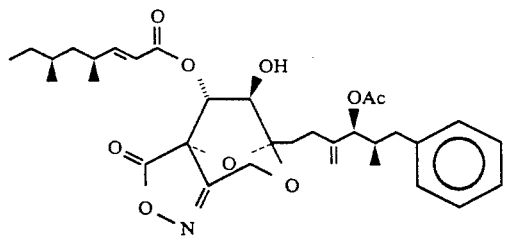

Hydroxylamine hydrochloride (5 mmol) and sodium acetate (10 mmol) are dissolved in a mixture of glacial acetic acid (2 mL) and water (1 mL). Composition A (0.2 mmol) dissolved in methanol (2 mL) is added to the above solution. The reaction mixture is stirred for one minute. It is then allowed to stand at room temperature for 2 hours to 2 days.

After the reaction the entire mixture is loaded onto the HP-20 column and the product is isolated as described in Example 2.

EXAMPLE 4

Preparation of the (C-4) O-methyl oxime of composition A, comprising a compound of the structure

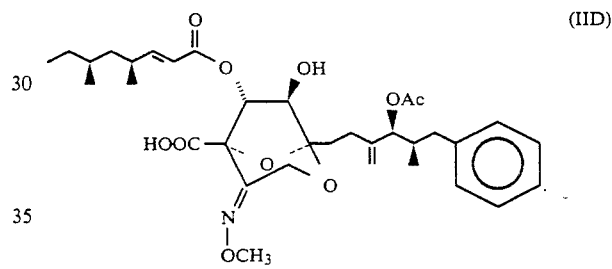
(IID)

O-Methylhydroxylamine hydrochloride (5 mmol) and sodium acetate (10 mmol) are dissolved in a mixture of glacial acetic acid (2 mL) and water (1 mL). Composition A (0.2 mmol) dissolved in methanol (2 mL) is added to the above solution. The reaction mixture is stirred for one minute. It is then allowed to stand at room temperature from between about 2 hours to an overnight incubation.

After the reaction the entire mixture is loaded onto the HP-20 column and the product is isolated as described in Example 2.

EXAMPLE 5

Preparation of the (C-4) O-ethyl oxime of composition A, comprising a compound of the structure

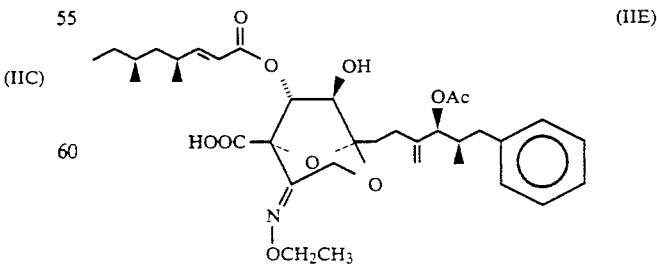
(IIE)

O-Ethylhydroxylamine hydrochloride (5 mmol) and sodium acetate (10 mmol) are dissolved in a mixture of glacial acetic acid (2 mL) and water (1 mL). Composition A (0.2 mmol) dissolved in methanol (2 mL) is added to the above solution. The reaction mixture is stirred for one minute. It is then allowed to stand at room temperature for between about 2 hours and an overnight incubation.

After the reaction the entire mixture is loaded onto the HP-20 column and the product is isolated as described in Example 2.

EXAMPLE 6

Preparation of the 4-methyl-4-hydroxyl derivative of composition A, comprising a compound of the structure:

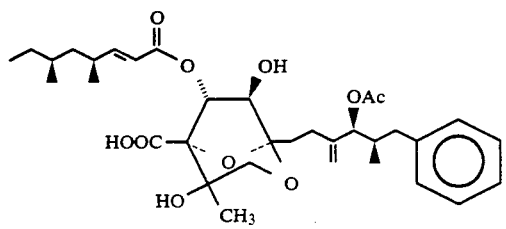

(IIF)

Composition A (0.1 mmol) is dissolved in anhydrous tetrahydrofuran (THF) (3 mL). Methylmagnesium iodide (5.5 mmol) dissolved in anhydrous THF (3 mL) or diethylether (3 mL) is added to the above solution. The reaction mixture is stirred for one minute then kept at room temperature for two hours. The entire procedure is carried out under Ar atmosphere. After the reaction 2N acetic acid (5 mL) is added to the mixture. The solution is concentrated down to dryness.

The residue is redissolved in methanol (4 mL). The methanol solution is filtered and loaded onto the HP-20 column for chromatographic separation according to the procedure of Example 2.

EXAMPLE 7

Preparation of the 4-ethyl-4-hydroxyl derivative of composition A, comprising a compound of the structure:

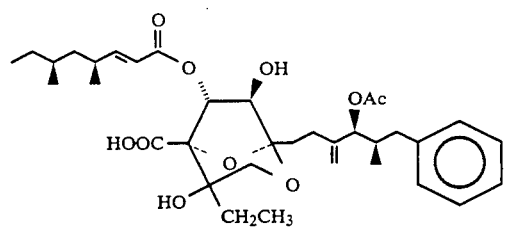

(IIG)

Composition A (0.1 mmol) is dissolved in anhydrous tetrahydrofuran (THF) (3 mL). Ethylmagnesium iodide (5.5 mmol) dissolved in anhydrous THF (3 mL) or diethylether (3 mL) is added to the above solution. The reaction mixture is stirred for one minute then kept at room temperature for two hours. The entire procedure is carried out under Ar atmosphere. After the reaction 2N acetic acid (5 mL) is added to the mixture. The solution is concentrated down to dryness.

The residue is redissolved in methanol (4 mL). The methanol solution is filtered and loaded onto the HP-20 column for chromatographic separation according to the procedure of Example 2.

EXAMPLE 8

Preparation of the 4-n-propyl-4-hydroxyl derivative of composition A, comprising a compound of the structure:

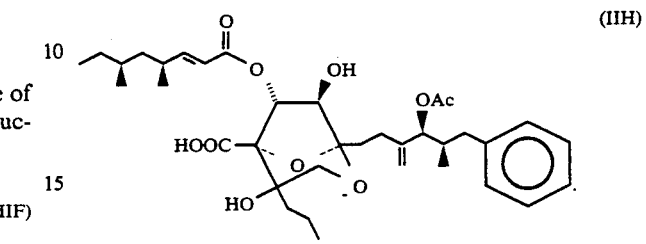

(IIH)

Composition A (0.1 mmol) is dissolved in anhydrous tetrahydrofuran (THF) (3 mL). A quantity of n-propylmagnesium iodide (5.5 mmol) dissolved in anhydrous THF (3 mL) or diethylether (3 mL) is added to the above solution. The reaction mixture is stirred for one minute then kept at room temperature for two hours. The entire procedure is carried out under Ar atmosphere. After the reaction 2N acetic acid (5 mL) is added to the mixture. The solution is concentrated down to dryness.

The residue is redissolved in methanol (4 mL). The methanol solution is filtered and loaded onto the HP-20 column for chromatographic separation according to the procedure of Example 2.

EXAMPLE 9

Preparation of the 4-cyanohydrin derivative of Composition A, comprising a compound of the structure:

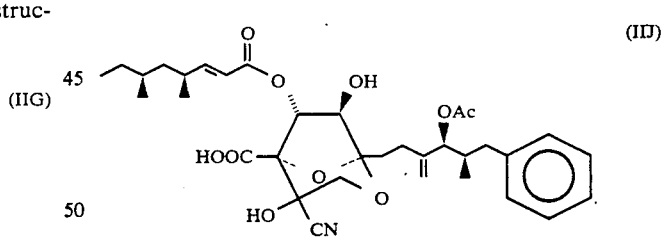

(IIJ)

Composition A (0.2 mmol) is dissolved in dimethylformamide (2 mL). KCN (2.5 mmol) dissolved in water (1 mL) is added to the above solution. The reaction components are mixed, then glacial acetic acid (0.5 mmol) is added. The reaction vessel is tightly closed and allowed to stand 2 hours at room temperature.

The entire solution is loaded onto the HP-20 column for chromatographic separation according to the procedure described under Example 2.

EXAMPLE 10

Preparation of a formula (I) compound of the structure

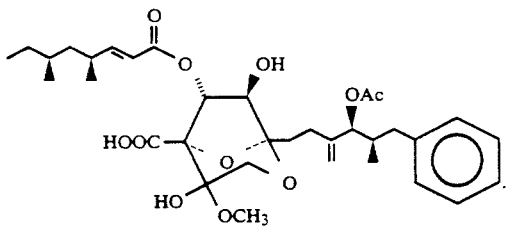

(IA)

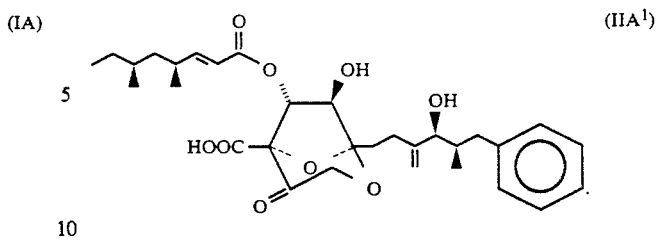

(IIA¹)

This compound (IA) was prepared by evaporating to dryness a sample of composition A from Example 1 and then dissolving the dried material in anhydrous methanol. A solution of (IA) was obtained substantially free of other equilibrium structures:

¹NMR (400 MHz) (CD₃OD) 4.06 (d, 13.1, 1H), 3.86 (d, 13.1, 1H) 3-CH₂ ¹³C NMR 170.8, 106.4, 93.8, 89.4, 82.8, 81.8, 63.4.

EXAMPLE 11

Preparation of a formula (II) compound of the structure

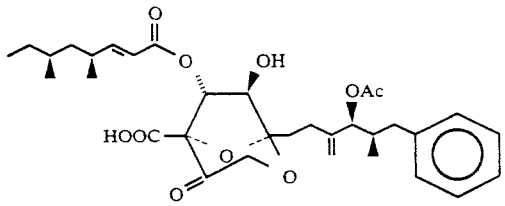

(IIA)

This compound (IIA) was prepared by evaporating to dryness a sample of composition A from Example 1 and then dissolving the dried material in pure acetone. A solution of (IIA) was obtained substantially free of other equilibrium structures.

¹H NMR (Acetone) 4.67 (d, 17.1, 1H), 4.42 (d, 17.1, 1H), 3-CH₂ ¹³C NMR (Acetone) 197.2, 163.5, 106.8, 91.9, 82.9, 80.8, 70.3.

EXAMPLE 12

Preparation of a formula (III) compound of the structure

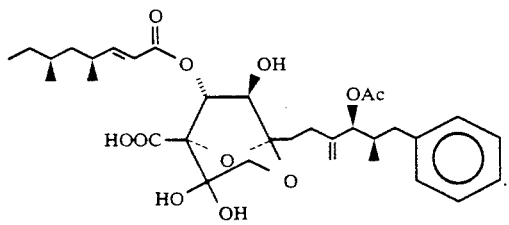

(IIIA)

This compound (IIIA) was prepared by adding to the acetone solution of Example 6 an amount of water to bring the water concentration to about 10%. A solution of IIIA was obtained substantially free of other equilibrium structures.

¹³C NMR (Acetone+D₂O) 169.7, 106.1, 90.3, 88.7, 82.5, 81.4, 70.0.

EXAMPLE 13

Preparation of a formula (I) compound comprising the structure

1. Seed Growth

Aliquots of medium #2 (50 mL) in 250 mL baffled flasks were inoculated with MA6817 and shaken in a rotary shaker at 200 rpm and 27° C. The seed was grown for 48 hours.

2. Fermentation

Production flasks (medium #2, 50 mL is 250 mL baffled flasks) were inoculated with 2 mL of the seed medium and shaken at 27° C. and 220 rpm on a rotary shaker. After 24 hours, a substrate containing a crude mixture of Zaragozic Acid A and Composition A, prepared above (Example 1), was added to each flask. Thus, a DMSO solution of the substrate containing Zaragozic Acid A (1.217 mg, 76.1%) and Composition A (0.382 mg, 23.9%) was used for each of two shake flasks. Incubation continued for 72 hours.

3. Extraction

The harvested biotransformation samples were acidified with formic acid (2 mL 88% for each flask) then extracted with ethyl acetate. The organic phase was dried over Na₂SO₄ then filtered and evaporated to dryness. The dry residue was redissolved in the smallest possible volume of DMSO-water (2:1 v/v) for preparative HPLC.

4. Chromatography

Two different gradient methods were used in succession. The first separation was accomplished on a Beckman Ultrasphere Cyano column (10×250 mm) in a gradient from 20% solvent B/80% solvent A to 65% solvent B/35% solvent A in 35 minutes then at 100% solvent B for an additional 10 minutes, at a flow rate of 3.00 mL/min. Fractions were collected every 3 minutes or according to peaks detected at 213 nm, as appropriate. The selected fractions (22.5–24.0 min) were evaporated to dryness and chromatographed again on a Beckman Ultrasphere Octyl column (10×250 mm) in a gradient from 30% B/70% A to 80% B/20% A in 35 minutes then at 100% solvent B for an additional 10 minutes, at a flow rate of 3.00 mL/min. The remaining conditions were the same as in the first separation. Solvent A was 20 mM HCOOH and B was acetonitrile-water (17:3 v/v) containing the same amount of HCOOH as solvent A.

Evaporation of the selected fractions (retention time 33.6 min.) provided the product, Compound (IIA1), with the following physical characteristics:

¹H NMR spectrum (400 mHz) (CD₃OD, 22° C.): 7.23 (t, 2H), 7.19 (d, 2H), 7.12 (t, 1H), 6.87 (dd, 15.7, 8.4, 1H), 5.86 (dd, 15.7, 1.0, 1H), 5.50 (d, 2.4, 1H), 5.06 (s, 1H), 4.93 (s, 1H), 4.01 (d, 2.4, 1H), 3.98 (d, 12.7, 1H), 3.89 (d, 5.0, 1H), 3.83 (d, 12.7, 1H), 2.75 (dd, 13.4, 5.9, 1H), 2.36 (dd, 13.4, 9.0, 1H), 2.0–2.45 (m, 4H), 1.93 (m, 2H), 1.1–1.4 (m, 5H), 1.03 (d, 3H), 0.86 (t, 3H), 0.85 (d, 3H), 0.79 (d, 3H) ppm.

Analytical HPLC on a Beckman Ultrasphere Ocytl column (4.6×250 mm) wherein the elution was performed in the gradient mode according to the following program:

| Solvent A: | 10 mM $H_3PO_4$ in water | |
|---|---|---|
| Solvent B: | Acetonitrile-water (85:15 v/v) | |
| Time (min.) | | percent B |
| 0 | | 30 |
| 2 | | 30 |
| 18 | | 80 |
| 20 | | 100 |
| 24 | | 100 |
| 25 | | 30 |
| Flow: | 0.900 mL/min | |
| Temp.: | Ambient | |

Retention time of Compound IIA1 = 19.9 minutes UV max at 213 nm.

EXAMPLE 14

Preparation of L-740, 790, which is a reduced derivative of Composition A, comprising the structure

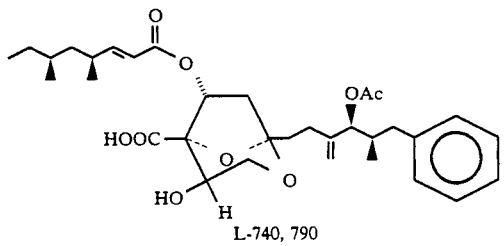

L-740, 790

Composition A (20 mg) was dissolved in 50/50 isopropanol:2N $NH_4Ac$ pH 4.5 (2.5 ml). About 20 mg of $NaBH_4$ was slowly added until the reaction was complete, as measured by analytical HPLC as follows:

Analytical HPLC was performed on a Beckman Ultrasphere Octyl column (4.6×250 mm) wherein the elution was performed in the gradient mode according to the following program:

| Solvent A: | 10 mM $H_3PO_4$ in water | |
|---|---|---|
| Solvent B: | Acetonitrile-water (85:15 v/v) | |
| Time (min.) | | percent B |
| 0 | | 40 |
| 2 | | 40 |
| 18 | | 100 |
| 24.5 | | 100 |
| Flow: | 0.900 mL/min | |
| Temp.: | Ambient | |

Retention time of L-740,790 = 19.3 minutes. The gem-diol reactant had a retention time of 18.3 minutes.

The reaction product mixture was then adjusted to pH 3.0 with crystalline citric acid. After adding one volume of water, extraction (3×) with 5 ml of ethyl acetate was carried out, then washing twice with $H_2O$, and drying. The residue was redissolved in 0.3 ml of methanol, then subjected to preparative HPLC as follows.

Preparative HPLC on a Beckman Ultrasphere Octyl column (10×250 mm) wherein the elution was performed in the gradient mode according to the following program:

| Solvent A: | 0.1% Formic Acid in water | |
|---|---|---|
| Solvent B: | 0.1% Formic Acid in Acetonitrile-water (85:15 v/v) | |
| Time (min.) | | percent B |
| 0 | | 70 |
| 19 | | 70 |
| 20.5 | | 100 |
| 30 | | 100 |
| Flow: | 4 mL/min | |
| Temp.: | Ambient | |

Retention time of L-740,790 = 21.4 minutes. The gem-diol reactant had a retention time of 9.4 minutes.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. A compound of formula V, of the structures

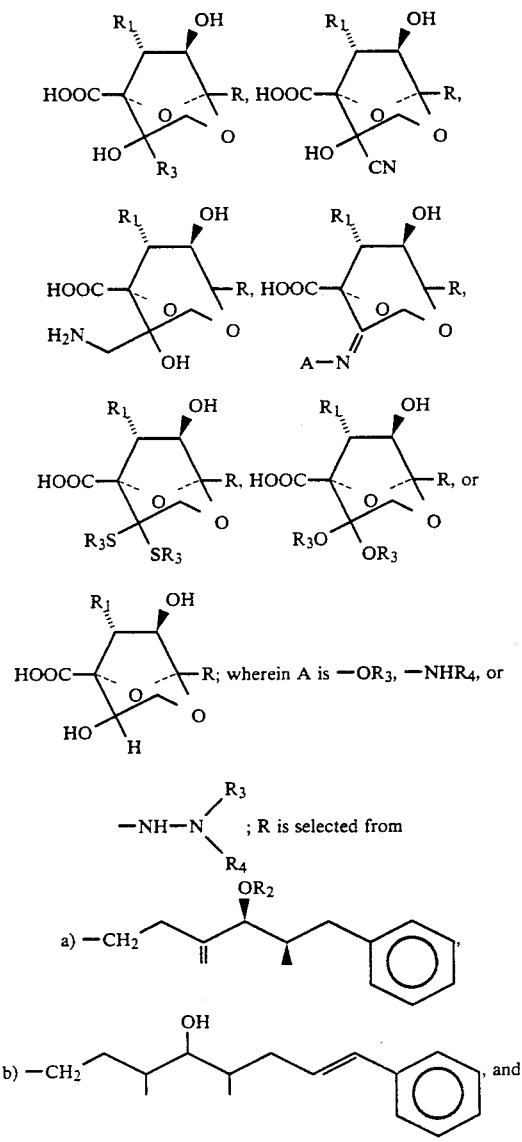

-continued

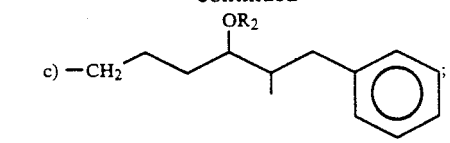

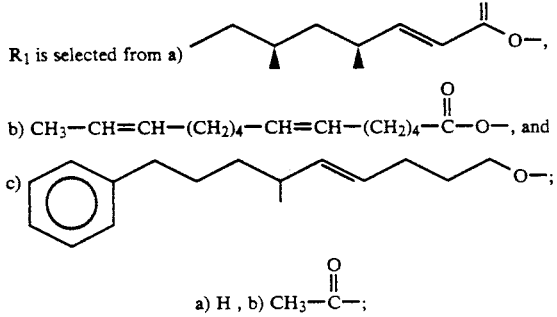

R₃ is H, C₁₋₄ alkyl;
R₄ is H, C₁₋₄ alkyl;
or pharmaceutically acceptable salts thereof,
provided that when R is

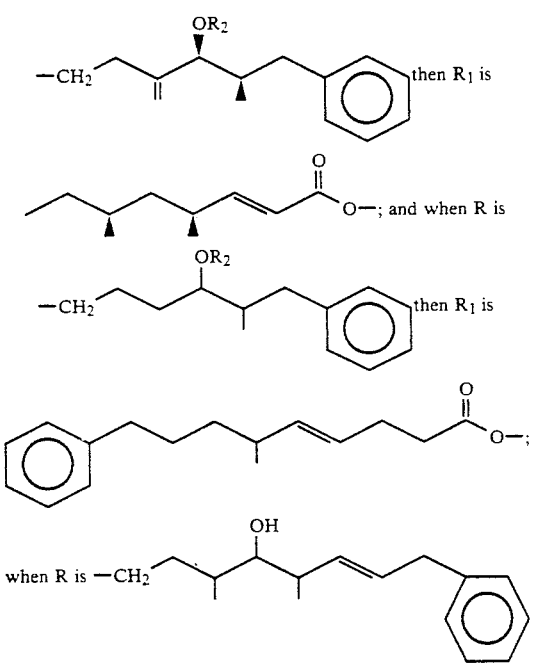

-continued then R₁ is CH₃—CH═CH—(CH₂)₄—CH═CH—(CH₂)₄—C(=O)—O—.

2. A compound according to claim 1, wherein formula V is

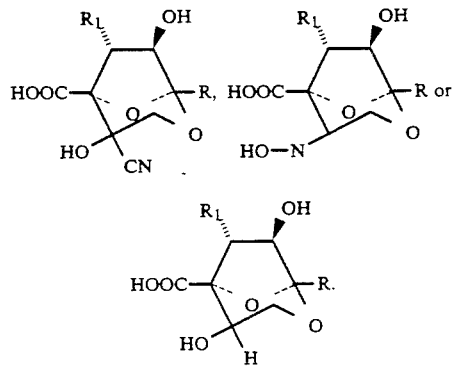

3. A compound according to claim 2, wherein formula V is

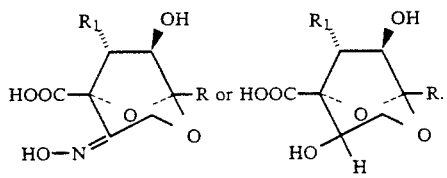

4. The compound L-740,790, of the structure

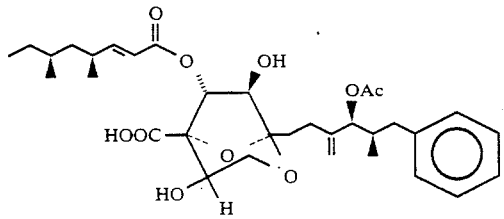

or pharmaceutically acceptable salts thereof.

5. A pharmaceutical composition comprising a nontoxic therapeutically effective amount of a compound as in any of claims 1-3, and a pharmaceutically acceptable carrier.

* * * * *